United States Patent
Saleh et al.

(10) Patent No.: US 9,452,418 B2
(45) Date of Patent: Sep. 27, 2016

(54) GOLD LOADED TIO2 NANOTUBE-MULTIWALLED CARBON NANOTUBE COMPOSITES AS ACTIVE PHOTOCATALYSTS FOR CYCLOHEXANE OXIDATION

(71) Applicant: UMM AL-QURA UNIVERSITY, Makkah (SA)

(72) Inventors: Saleh Abdel-Mgeed Ahmed Saleh, Makkah (SA); Mohamed Mokhtar Mohamed Abdalla, Benha (EG); Khalid Soliman Khalil Khairou, Makkah (SA)

(73) Assignee: Umm Al-Qura University, Makkah (SA)

( * ) Notice: Subject to any disclaimer, the term of this patent is extended or adjusted under 35 U.S.C. 154(b) by 0 days.

(21) Appl. No.: 14/419,103

(22) PCT Filed: Jan. 23, 2015

(86) PCT No.: PCT/IB2015/000067
§ 371 (c)(1),
(2) Date: Feb. 2, 2015

(87) PCT Pub. No.: WO2016/116776
PCT Pub. Date: Jul. 28, 2016

(65) Prior Publication Data
US 2016/0214087 A1  Jul. 28, 2016

(51) Int. Cl.
| | | |
|---|---|---|
| C07C 45/00 | (2006.01) |
| B01J 23/48 | (2006.01) |
| B01J 21/06 | (2006.01) |
| B01J 21/18 | (2006.01) |
| B01J 35/02 | (2006.01) |
| B01J 35/10 | (2006.01) |
| B01J 37/02 | (2006.01) |
| B01J 37/34 | (2006.01) |
| C07C 45/29 | (2006.01) |

(52) U.S. Cl.
CPC ............. *B01J 23/48* (2013.01); *B01J 21/063* (2013.01); *B01J 21/185* (2013.01); *B01J 35/023* (2013.01); *B01J 35/1014* (2013.01); *B01J 35/1019* (2013.01); *B01J 35/1038* (2013.01); *B01J 37/0215* (2013.01); *B01J 37/343* (2013.01); *C07C 45/294* (2013.01); *C07C 2101/14* (2013.01)

(58) Field of Classification Search
CPC ...... C07C 45/294; B01J 23/48; B01J 21/063

USPC ......................................................... 568/342
See application file for complete search history.

(56) References Cited

U.S. PATENT DOCUMENTS
2015/0050494 A1   2/2015 Yeung et al.

FOREIGN PATENT DOCUMENTS
| | | |
|---|---|---|
| CN | 101972641 A | 2/2011 |
| CN | 102828219 | 12/2012 |
| CN | 103657646 A | 3/2014 |
| JP | 2009-249206 | 10/2009 |
| KR | 10-2013-0025475 A | 3/2013 |
| WO | WO 2013/139174 A1 | 9/2013 |

OTHER PUBLICATIONS

International Search Report and Written Opinion issued Oct. 26, 2015 in PCT/IB2015/000067.
Li, H. J., "Electrochemical application of titanium dioxide nanoparticle/gold nanoparticle/multiwalled carbon nanotube nanocomposites for nonenzymatic detection of ascorbic acid", Journal of Solid State Electrochemistry, vol. 18, Issue 2, pp. 477-485, Feb. 2014, (9 pages).
Wang, H. H. et al., "Enhancing the photocatalytic properties of TiO2 by coupling with carbon nanotubes and supporting gold", Journal of Hazardous Materials, vol. 235-236, pp. 230-26, Oct. 2012, ( 2 pages).
Zhang, Y. X. et al., "Self-Assembled Au/TiO2/CNTs Ternary Nanocomposites for Photocatalytic Applications", Science of Advanced Materials, vol. 2, No. 4, pp. 503-513(11), Dec. 2010 , (1 page).
Lixia, Y. et al., "Carbon-Nanotube-Guiding Oriented Growth of Gold Shrubs on TiO2 Nanotube Arrays", The Journal of Physical Chemistry, vol. 114, No. 17, pp. 7694-7699, Apr. 2010, ( 4 pages).

*Primary Examiner* — Sikarl Witherspoon
(74) *Attorney, Agent, or Firm* — Oblon, McClelland, Maier & Neustadt, L.L.P.

(57) ABSTRACT

A gold/titanium nanotube-multiwalled carbon nanotube composite (Au/TNT-MWCNT) is presented. The gold composition comprises at least 3% weight of the nanotube composite based on the total weight of the nanotube composite and the gold composition is located in at least one of the wall of the titanium nanotube and the wall of the multiwalled carbon nanotube. Photocatalytic oxidation of neat cyclohexane (CHA) with $H_2O_2$ as an oxidant was carried out. Au/TNT-MWCNT catalysts promoted partial CHA oxidation with high conversion (6-7.5%) and selectivity (60-75%) to cyclohexanone.

9 Claims, 7 Drawing Sheets

GOLD LOADED TIO2 NANOTUBE-MULTIWALLED CARBON NANOTUBE COMPOSITES AS ACTIVE PHOTOCATALYSTS FOR CYCLOHEXANE OXIDATION

BACKGROUND OF THE INVENTION

1. Technical Field

The present disclosure relates to a gold/titanium nanotube-multiwalled carbon nanotube composite, a method of making the gold/titanium nanotube-multiwalled carbon nanotube composite, and a method for the oxidation of cyclohexane wherein the nanotube composite is a catalyst in the oxidation.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Titanium oxide nanotubes ($TiO_2$ nanotube, TNT) are nanostructured oxides having tubular shapes with almost no absorption in the visible light region (S. Iijima, Nature 354 (1991) 56-58—herein incorporated by reference in its entirety). UV light-sensitive chemical reactions occur at the surface of the nanotube (N. G. Chopra, R. J. Luyken, K. Cherrey, V. H. Crespi, M. L. Cohen, S. G. Louie, A. Zettl, Science 269 (1995) 966-968—herein incorporated by reference in its entirety). Researchers have fabricated a variety of geometric structures of $TiO_2$ nanoparticles including zero dimensional (0D) structures such as spheric nanoparticle (Y. Feldman, E. Wasserman, D. J. Srolovitz, R. Tenne, Science 267 (1995) 222-225; M. E. Spahr, P. Bitterli, R. Nesper, M. Müler, F. Krumeich, H. U. Nissen, Angew. Chem. Int. Ed. 37 (1998) 1263-1265—each incorporated herein by reference in its entirety), and one-dimensional (1D) structures such as nanowires (P. M. Ajayan, O. Stephan, Ph. Redlich, C. Colliex, Nature 375 (1995) 564-567; B. C. Satishkumar, A. Govindaraj, E. M. Vogl, L. Basumallick, C. N. R. Rao, J. Mater. Res. 12(3), (1997) 604-606—each incorporated herein by reference in its entirety), nanorods (H. Nakamura, Y. Matsui, J. Am. Chem. Soc. 117(9), (1995) 2651-2652—incorporated herein by reference in its entirety), nanobelts (P. Hoyer, Langmuir 12 (1996) 1411-1413; T. Kasuga, M. Hiramatsu, A. Hoson, T. Sekino, K. Niihara, Langmuir 14 (1998) 3160-3163—each incorporated herein by reference in its entirety) or nanotubes (T. Kasuga, M. Hiramatsu, A. Hoson, T. Sekino, K. Niihara, Adv. Mater. 11 (1999) 1307-1311; D. Gong, C. A. Grimes, O. K. Varghese, W. Hu, R. S. Singh, Z. Chen, E. C. Dickey, J. Mater. Res. 16 (2001) 3331-3334—each incorporated herein by reference in its entirety). The titanium oxide nanotube is mainly useful in dealing with waste-water due to the large surface to volume ratio. This improves the photocatalytic activity compared with spherical particles under UV-Vis irradiation. Numerous efforts have been developed to fabricate $TiO_2$ nanoscale materials with special morphologies by employing traditional methods such as, sol-gel, micelle, and hydrothermal or solvothermal methods (H. Masuda, K. Nishio, N. Baba, Jpn. J. Appl. Phys. 31 (1992) L1775-L1777; P. Hoyer, Langmuir 12 (1996) 1411-1413—each incorporated herein by reference in its entirety). In general, one main drawback of the $TiO_2$ nanostructures, when used in the practical application, comes from their easy loss during the process of water treatment. This results in low utilization rate and high cost, which limits their widespread use. Some attempts have been employed to improve the reuse efficiency of $TiO_2$ via immobilization onto some supports such as carbon nanotube (B. O'Regan, M. Grätzel, Nature 353 (1991) 737-739; S. Hasegawa, Y. Sasaki, S. Matsuhara, Sens. Actuator B 13-14 (1993) 509-510—each incorporated herein by reference in its entirety), glass (G. H. Du, Q. Chen, R. C. Che, Z. Y. Yuan, L. M. Peng, Appl. Phys. Lett. 79 (2001) 3702-3704—incorporated herein by reference in its entirety), ceramic (Q. H. Zhang, L. A. Gao, J. Sun, S. Zheng, Chem. Lett. 31 (2002) 226-227—incorporated herein by reference in its entirety), and activated carbon (S. X. Liu, X. Y. Chen, X. Chen, Journal of Hazardous Material, vol. 143 (2007) 257-263; T. T. Lim, P. S. Yap, M. Srinivasan, A. Fane, Critical Reviews in Environmental Science and Technology, 41 (2011) 1173-1230; R. Kumar, S. K. Sithambaram, S. L. Suib, Journal Catalysis 262 (2009) 304-313—each incorporated herein by reference in its entirety). However, the current immobilization techniques are still not stable enough to improve the reaction efficiency due to decreasing $TiO_2$ dispersion as well as its leaching from the supports. Among the previous supports, nanocarbon particles were chosen because they may increase remarkably the photoactivity of $TiO_2$. Use of nanocarbon materials was found to provide attractive properties including exceptional electronic, adsorption, chemical inertness and stability (H. Slimen, A. Houas, J. P. Nogier, Journal of Photochemistry photobiology A: Chemistry, 221 (2011) 13-21; Y. Suzuki, S. Yoshikawa, J. Mater. Res. 19 (2004) 982-985; B. Seger, P. V. Kamat, J. Phys. Chem. C 113 (2009) 7990-7995; K. Woan, G. Pyrgiotakis, W. Sigmund, Advanced Materials 21(2009) 2233-2239—each incorporated herein by reference in its entirety). In recent studies (G. Socol, Yu. Gnatyuk, N. Stefan, N. Smirnova, V. Djokic', C. Sutan, V. Malinovschi, A. Stanculescu, O. Korduban, I. N. Mihailescu, Thin Solid Films 518 (2010) 4648-4653; R. Leary, A. Westwood, Carbon 49 (2011) 741-772; K. A. Wepasnick, B. A. Smith, K. E. Schrote, H. K. Wilson, S. R. Diegelman, D. H. Fairbrother, Carbon 49 (2011)24-36—each incorporated herein by reference in its entirety), attention was paid to the fact that $TiO_2$ is an n-type semiconductor and the major process in photocatalysis is activated by photon absorption and electron—hole formation. An enhancement of the photocatalytic properties of $TiO_2$ can be accomplished via functionalization with CNT that hinders electron—hole pair recombination. In this way, $TiO_2$ effectively behaves as a p-type semiconductor in the $TiO_2$/CNT nanocomposites. Additionally, the large number of active adsorption sites at the catalyst surface and the improved suppression of the recombination of the charge carriers contribute to increasing photocatalytic activity. Many specific methods for the synthesis of $TiO_2$/CNT nanocomposites have been developed, which generally consist of two steps: functionalization of the CNT and the nanocomposite synthesis. One of the functionalization methods applied to CNT is oxidative treatment, upon which the nanotubes become shortened, less tangled with ends opened, and oxygen-containing functional groups are introduced on their surfaces. The mentioned groups have a pronounced effect on the surface properties of the carbonaceous material, providing numerous sites for $TiO_2$ bonding (J. P. Chen, S. Wu, Langmuir 20 (2004) 2233-2242; A. J. Plomp, D. S. Su, K. P. deJong, J. H. Bitter, Journal of Physical Chemistry C 113 (2009) 9865-9869; H. F. Gorgulho, J. P. Mesquita, F. Gonc-alves, M. F. R. Pereira, J. L. Figueiredo, Carbon 46 (2008) 1544-1555—each incorporated herein by reference in its entirety). The preparation and use of a $TiO_2$/nanocarbon composite photocatalyst by coating anatase $TiO_2$ having a nanospindle structure onto the oxidized surface of multi-wall carbon nanotubes (MWCNT) and the use of the resulting composite for photocatalytic cyclohexane oxidation was described.

Assembling metal particles either in the wall of titania and/or in carbon nanotubes or both will enhance their photoelectricity, electromagnetism and catalytic properties. Gold catalysts have been successfully used for cyclohexane oxidation based on various supports including metal oxides (M. Conte, X. Liu, D. M. Murphy, K. Whiston, G. J. Hutchings, Phys. Chem. Chem. Phys. 14 (2012) 16279-16285—incorporated herein by reference in its entirety), metal organic frameworks, (Z. G. Sun, G. Li, L. P. Liu, H. O. Liu, Catal. Commun. 27 (2012) 200-205—incorporated herein by reference in its entirety) mesoporous silica (L.-X. Xu, C.-H. He, M.-Q. Zhu, K.-J. Wu, Y.-L. Lai, Catal. Commun. 9 (2008) 816-820; X. Jiang, H. Deng, X. Wang, Colloid Surf. A: Physicochem. Eng. 358 (2010) 122-127; J. Xie, Y. Wang, Y. Li, Y. Wei, React. Kinet. Mech. Catal. 102 (2011) 143-154—each incorporated herein by reference in its entirety) based materials, and hydroxyapatite (Y. Liu, H. Tsunoyama, T. Akita, S. Xie, T. Tsukuda, ACS Catal. 1 (2011) 2-6—incorporated herein by reference in its entirety). It has been questioned whether gold catalysts actually do act as catalysts or as promotors of the autoxidation reaction (C. Della Pina, E. Falletta, M. Rossi, Chem. Soc. Rev. 41 (2012) 350-369—incorporated herein by reference in its entirety). Some authors support that gold acts as a catalyst for this reaction (A. Alshammari, A. Koeckritz, V. N. Kalevaru, A. Bagabas, A. Martin, Chem-Cat Chem 4 (2012) 1330-1336—incorporated herein by reference in its entirety) whereas others concluded that it works via a pure radical pathway with products typical of autoxidation (B. P. C. Hereijgers, B. M. Weckhuysen, J. Catal. 270 (2010) 16-25—incorporated herein by reference in its entirety). In general, Au/oxide studies were performed at high temperatures (above 373 K) and at oxygen pressures ranging from 0.3 to 3 MPa, with no solvent. On the other hand, titanium based catalysts like titanium silicalite-1 and Ti-MCM-41 when used with $H_2O_2$ presented low conversion for cyclohexane (E. V. Spinace, H. O. Pastore, U. Schuchardt, J. Catal. 157 (1995) 631-639; W. A. Carvalho, P. B. Varaldo, M. Wallau, U. Schuchardt, Zeolites 18 (1997) 408-412—each incorporated herein by reference in its entirety). V- and Cr-MCM-41 gave higher activities compared to Ti-MCM-41, however all metallosilicates undergo leaching of the metal and the observed catalytic activity was mainly due to the leached homogeneous metal species. Although $H_2O_2$ is environmentally friendly since it produces water as the only by-product, the major disadvantage of $H_2O_2$ is the instability that permits its decomposition into oxygen and water, a process which is accelerated in the presence of transition metal complexes and metal oxides (G. Strukul, Catalytic Oxidations with Hydrogen Peroxide as Oxidant, Kluwer Academic Publishers, Dordrecht, 1992—incorporated herein by reference in its entirety). The disadvantages like low conversion, leaching of metal, and over-oxidation products in existing catalytic systems have led researchers to find a catalyst that can improve the conversion of cyclohexane under ambient conditions, with high selectivity to cycloexanone/cyclohexanol ratio.

In view of finding a way for overcoming the above-mentioned obstacles, titanium nanotube photoatalysts synthesized by hydrothermal method incorporated with MWCNT and loaded with gold are tested in the selective photo-oxidation of cyclohexane, for evaluating the effect of surface modification as well as morphology on the catalysts' behavior. This is attained via using the versatile and green oxidant $H_2O_2$ to avoid using traditionally oxidizing agent; such as $CrO_4^{2-}$, $MnO_4^-$ and $ClO_4^-$, that produce toxic by-products.

The present disclosure describes a gold loaded TNT and TNT-MWCNT composition. Gold loaded TNT and TNT-MWCNT is synthesized and tested for cyclohexane oxidation. Feactors contributing to the enhanced catalytic activity are identified. For comparison purposes, Au/graphene was synthesized and tested for cyclohexane oxidation to determine the effect of graphene's higher conductivity and large surface area (S. Gilje, S. Han, M. Wang, K. L. Wang, R. B. Kaner, Nano Lett. 7 (2007) 3394-3398; R. Pasricha, S. Gupta, A. K. Srivastava, Small 5 (2009) 2253-2259—each incorporated herein by reference in its entirety) on the activity performance.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure describes a gold/titanium nanotube-multiwalled carbon nanotube composite.

In another embodiment gold (Au) comprises 2-4 weight % of the nanotube composite.

In another embodiment the Au is located in at least one of the walls of the titanium nanotube and the walls of the multiwalled carbon nanotube.

In another embodiment the nanotube composite comprises 30-40% of the multi-walled carbon nanotube by weight of the total weight of the titanium nanotube.

In another embodiment the multiwalled carbon nanotube and 60-70% of the titanium nanotube by weight of the total weight of the titanium nanotube and multiwalled carbon nanotube.

In another embodiment the gold titanium nanotube-multiwalled carbon nanotube has an average particle diameter of 10-20-nm.

In another embodiment the gold titanium nanotube-multiwalled carbon nanotube has a surface area of 50-500 $m^2/g$.

In another embodiment the gold titanium nanotube-multiwalled carbon nanotube has a pore volume of 0.180-0.199 $cm^3/g$.

In another embodiment the gold titanium nanotube-multiwalled carbon nanotube has a spindle shape.

Another embodiment describes a method of making the gold/titanium nanotube-multiwalled carbon nanotube.

In another embodiment the method comprises coating anatase $TiO_2$ having a nanospindle structure onto an oxidized surface of a multi-wall carbon nanotube.

In another embodiment the method comprises contacting the multi-walled carbon nanotube with gold in the wall of titania and/or in the carbon nanotube.

Another embodiment describes a method for oxidation of cyclohexane.

In another embodiment the method for oxidation of cyclohexane comprises reacting cyclohexane in a photocatalytic oxidation reaction.

In another embodiment the method for oxidation of cyclohexane uses $H_2O_2$ as an oxidant.

In another embodiment the gold/titanium nanotube-multiwalled carbon nanotube is a catalyst for the oxidation of cyclohexane.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

Synthesis of TNT

One embodiment of the disclosure includes a method of making a titania nanotube (TNT). First $TiO_2$ anatase is refluxed under basic conditions in the presence of a base such as NaOH. The $TiO_2$ anatase is refluxed at a temperature in the range of 350-550 K, 375-525 K, or 400-500 K. The anatase $TiO_2$ is present in a basic solution in an amount of 1 g/67 mL NaOH—2 g/133 mL NaOH, 1.2 g/80 mL NaOH—1.8 g/120 mL NaOH or 1.3 g/87 mL NaOH—1.8 g/120 mL NaOH. The $TiO_2$ anatase is refluxed with the NaOH solution for a time period in the range of 10-40 hours, 20-30 hours, or 22-28 hours. Preferably 1.5 g $TiO_2$ anatase is refluxed at 423 K with 100 ml 10 M NaOH solution for 24 hours. The suspension formed from the reflux reaction is filtered and washed with an aqueous acidic solution and distilled water. The aqueous acidic solution is preferably aqueous HCl. The aqueous acidic solution has a concentration in the range of 0.10-0.20 M, 0.12-0.18 M, or 0.14-0.16 M. Preferably the aqueous acidic solution has a concentration of 0.15 M. The resulting suspension is then dried at a temperature in the range of 250-450 K, 300-400 K, or 325-375 K for a time period in the range of 5-20 hours, 8-15 hours, or 9-14 hours. Preferably the suspension is dried at a temperature of 373 K for 10 hours. The suspension is then heated at a temperature in the range of 550-750 K, 575-675 K, or 600-650 K at a time period in the range of 2-15 hours, 3-14 hours, or 4-10 hours. Preferably the suspension is heated at a temperature in the range of 623 K for 6 hours.

Synthesis of Gold Supported on Titania Nanotube

Another embodiment of the invention includes a method of making a gold supported titania nanotube (Au/TNT) composite. First, an acid comprising gold, hydrogen and a halogen is dissolved in deionized water. The gold acid includes but is not limited to $HAuCl_4$, $HAuBr_4$, or $HAuI_4$. Preferably the acid is $HAuCl_4$. The concentration of the gold acid in the deionized water is in the range of from 1:100, preferably 5:100, 10:100, or 20:100 parts based on the total parts of gold acid and total parts of water. The mixture of the acid and the deionized water is poured onto TNT in a schlenk tube while stirring. The amount of TNT used is in the range of 1 g/67 mL solution—2 g/133 mL solution, 1.2 g/80 mL solution—1.8 g/120 mL solution or 1.3 g/87 mL solution—1.8 g/120 mL solution. Then $Na_2S$ is added to the mixture in an amount in the range of 5 mL/50 mL solution 100 mL/1000 mL solution, 6 mL/60 mL solution—50 mL/500 mL solution, or 7 mL/70 mL solution—40 mL/400 mL solution. $Na_2S$ is added in a drop wise manner until the color of the mixture changes from yellow to golden brown. A PVP aqueous solution is then added to stabilize the mixture in which the mixture changes to a faint rose color. PVP is added in an amount in the range of 5-25 ml, 10-20 ml, or 12-18 ml. Preferably 15 ml of PVP is added per 100 mL solution. The mixture is then washed and then. The dried mixture is then heated at a temperature in the range of 500-800 K, 575-725 K, or 600-700 K for a time period in the range of 1-10 hours, 2-8 hours, or 3-7 hours. Preferably the mixture is heated at a temperature of over 600 K for 6 hours.

Acid Treatment of MWCNT

Another embodiment of the invention includes a method of making a functionalized multi-walled carbon nanotube (MWCNT). First a MWCNT is dispersed in an acidic solution to form a mixture. MWCNT is added in an amount in the range of 0.5-2 g, 0.7-1.5 g, or 0.8-1.2 g. Preferably 1.0 g MWCNT is dispersed in 10-100 mL of the acidic solution. Preferably the acidic solution is a solution comprising $HNO_3$ in an amount in the range of 20-60 ml, 25-55 ml, or 30-50 ml at a concentration in the range of 40-70%, 50-68%< or 60-67%. Preferably the $HNO_3$ solution is at a volume of 40 ml and a concentration of 65%. The mixture is then agitated in an ultrasonic bath to form a suspension. The mixture is agitated at a temperature in the range of 250-450 K, 275-400 K, or 300-350 K for a time period in the range of 10-50 minutes, 20-40 minutes, or 25-35 minutes. Preferably the mixture is agitated at 314 K for 30 minutes. The suspension is then transferred to a Teflon lined stainless steel autoclave and stored at a temperature in the range of 300-500 K, 350-450 K, or 375-400 K at a time period in the range of 20-40 hours, 22-30 hours, or 23-28 hours. After storage a grey precipitate forms. The precipitate is then centrifuged and washed with aqueous HCl at a concentration in the range of 0.05-0.2 M, 0.08-1.5 M. or 0.09-1.2 M. The precipitate is also centrifuged with anhydrous ethanol to remove any organic species. The precipitate is then dried, preferably the precipitate is dried at 343 K for 12 hours.

Synthesis of MWCNT-TNT and Au/MWCNT-TNT Nanocomposites

Another embodiment of the invention includes a method of making a MWCNT-TNT nanocomposite and an Au/MWCNT-TNT nanocomposite. The functionalized MWCNT is dispersed in an aqueous solution to form a mixture. The mixture is then poured onto TNT and sonicated for a time period in the range of 15-40 minutes, 20-35 minutes, or 22-28 minutes at a temperature in the range of 250-350 K, 275-325 K, or 300-320 K. A suspension is formed from the sonication. The suspension is then autoclaved at a temperature in the range of 300-450 K, 325-425 K, or 350-400 K at a time period in the range of 10-20 hours, 12-18 hours, or 13-17 hours. A composite is formed comprising MWCNT and TNT. MWCNT and TNT are present in the resulting composition amounts of from 10% to 90% by weight based on the total weight of the composition. Preferably the MWCNT and TNT are present in relative amounts with respect to one another of 10% MWCNT and 90% TNT, 20% MWCNT and 80% TNT, 30% MWCNT and 70% TNT, or 50% MWCNT and 50% TNT, or 90% MWCNT and 10% TNT, 80% MWCNT and 20% TNT, 70% MWCNT and 30% TNT. Preferably the composition is 30% MWCNT and 70% TNT. The composition is then filtered and washed with deionized water and vacuum dried. Preferably the composition is vacuum dried at 343 K for 2 hours. The composition is then heat treated in air at a temperature in the range of 575-700 K 580-650 K, or 600-640 K at a time period in the range of 2-10 hours, 3-9 hours, or 4-8 hours. Preferably the composition is heat treated in air at 623 K for 6 hours. The MWCNT-TNT composite is produced after heat treatment. The MWCNT-TNT solution is then sonicated at a temperature in the range of 200-400 K, 250-350 K, or 275-325 K for a time period in the range of 30 minutes-2.5 hours, 45 minutes—1.25 hours, or 50 minutes—1.15 hours. Preferably the MWCNT-TNT solution is sonicated at a temperature of 298 K for 1 hour. The MWCNT-TNT solution is dissolved in an aqueous solution at a volume in the range of 25-100 ml, 30-75 ml, or 40-60 ml. Preferably the aqueous solution has a volume of 50 ml water. A solution comprising $HAuCl_4$ in an effective amount to produce a composition comprising at least 3% wt Au composite is added drop wise to the MWCNT-TNT and aqueous solution suspension. The suspension is then reduced via hydrazine hydrate for the reduction of Au ions. Preferably 100% of Au ions are reduced. The suspension is then heated at a temperature in the range of 250-450 K, 275-425 K, or 300-350 K at a time period in the range of 30 minutes—2.5 hours, 45 minutes—2 hours, or 50 minutes to 1.5 hours. Preferably the suspension is heated at 333 K for 1 hour until evaporation. The suspension is then left overnight at a temperature in the range of 250-450 K, 275-425 K, or 300-400 K. The suspension is then annealed at a temperature in the range of 500-700 K, 550-650 K, or 600-645 K at a time period in the range of 2-6 hours, 2.5-5.5 hours, or 3-4.5 hours. Preferably the suspension is annealed at over 600 K for 4 hours.

Cyclohexane Oxidation

Another embodiment of the invention includes a method for the oxidation of cyclohexane. First an effective amount of the catalyst and 10 mmole of cyclohexane is put into a photochemical reactor. Preferably the catalyst is the Au/MWCNT-TNT nanocomposite in an amount of 0.05 g. The photochemical reactor contains acetonitrile in an amount of 2-20 ml, 4-18 ml, or 6-15 ml. The photochemical reactor is fitted with a cooling jacket. $H_2O_2$ in an amount of 10 mmole is added via titration and poured into the system continuously and sealed by a rubber septum cap. Samples are then collected every hour after switching on the lamp for a total photo-oxidation period of preferably 12 hours. A UV lamp is placed horizontally inside the UV chamber.

Properties of the Nanocomposite

The Au/MWCNT-TNT nanocomposite comprises Au in an amount in the range of 1-10%, 1.5-9% or 2-5% based on the total weight of the nanocomposite. Preferably the Au/MWCNT-TNT nanocomposite comprises about 3% Au. The Au/MWCNT-TNT composite comprises 30-40% by weight of the multi-walled carbon nanotube by weight of the total weight of the titanium nanotube and multiwalled carbon nanotube, and 60-70% by weight of the titanium nanotube by weight of the total weight of the titanium nanotube and multiwalled carbon nanotube. Preferably the Au/MW-CNT-TNT composite comprises about 30% of the multi-walled carbon nanotube by weight and 70% of the titanium nanotube. The Au/MWCNT-TNT nanocomposite has an average particle diameter in the range of 10-20 nm, 12-18 nm, or 14-16 nm. Preferably the Au/MWCNT-TNT nanocomposite has an average particle diameter of about 15 nm. The Au/MWCNT-TNT nanocomposite has a surface area in the range of 50-500 $m^2/g$, 100-400 $m^2/g$, or 150-300 $m^2/g$. Preferably the Au/MWCNT-TNT nanocomposite has a surface area of 185-200 $m^2/g$. The Au/MWCNT-TNT nanocomposite has a pore volume in the range of 0.180-1.00 $cm^3/g$, 0.185-0.198 $cm^3/$, or 0.190-0.194 $cm^3/g$. Preferably the Au/MWCNT-TNT nanocomposite has a pore volume of 0.190-0.194 $cm^3/g$. The Au/MWCNT-TNT may have a shape of including but not limited to a fiber, a spheroid, or a spindle. Preferably the Au/MWCNT-TNT has a spindle shape.

EXAMPLES

Synthesis of Titania Nanotubes (TNT)

1.5 g of $TiO_2$ anatase (Aldrich) was refluxed at 423 K with 100 ml 10 M NaOH solution for 24 h. This milky suspension was then filtered and washed with aqueous HCl (0.15 M) and distilled water till pH 7 and dried at 373 K for 10 h and finally heated at 623 K for 6 h.

Synthesis of Gold Supported on Titania Nanotube

A specific amount of $HAuCl_4$ dissolved in deionized water was poured onto 1.5 g TNT in a schlenk tube whilst stirring. To this mixture, 10 ml of 0.1 M $Na_2S$ was added in a drop wise manner by which the colour changes from yellow to golden brown. 15 ml of PVP (10 g/100 ml) aqueous solution was added to stabilize the final faint rose colour. This mixture was then washed, evaporated at 324 k for 4 h and then heated at 623 K for 6 h.

Acid Treatment of MWCNT 1 g MWCNT (manufacture data: purity>95; diameter<8 nm; length 10-30 μm; $S_{BET}$>500 $m^2/g$) was dispersed in 40 ml 65% $HNO_3$ followed by agitation at 314 K for 30 min in an ultrasonic bath. This suspension was then transferred into a Teflon lined stainless steel autoclave and stored at 393 k for 24 h, producing a grey precipitate. This precipitate was centrifuged and washed with aqueous HCl (0.1 M); to remove metal impurities, as well as with anhydrous ethanol to remove organic species followed by drying at 343 K for 12 h.

Synthesis of MWCNT-TNT and Au/MWCNT-TNT Nanocomposites

The functionalized MWCNT dispersed in 50 ml deionized water was poured onto TNT and sonicated for 25 min at 314 K. This suspension was autoclaved at 373 K for 16 h to give a composite comprised of 30% MWCNT and 70% TNT. The suspension was then filtered and washed thoroughly with deionized water. Then, vacuum dried at 343 K for 2 h and finally heat treated in air at 623 K for 6 h to give the MWCNT-TNT composite. An enough amount of $HAuCl_4$ solution; to prepare 3 wt % Au, was added in a drop wise manner onto the suspension of MWCNT-TNT dissolved in 50 ml water; previously sonicated at 298 K for 1 h, followed by stirring for 1 h at room temperature. This suspension was then reduced via hydrazine hydrate to accomplish complete reduction of Au ions. This suspension was then heated at 333 K for 1 h till evaporation and left overnight at 373 K and finally annealed at 623 K for 4 h.

Synthesis of Graphene-oxide Supported Gold Nanoparticles

Graphene oxide functionalized by COOH and OH groups using the modified Hummers method was synthesized. More details about graphene oxide synthesis can be found elsewhere (M. M. Mohamed, M. S. El-Sharif, Applied Catalysis B: Environ. 142-143 (2013) 432-441—incorporated herein by reference in its entirety). An adequate amount of $HAuCl_4$ solution; to prepare 3 wt % Au, was added in a drop wise manner onto a suspension of graphene oxide (GO) dissolved in 50 ml water followed by stirring for 1 h at room temperature. This suspension was then reduced via using hydrazine hydrate to achieve complete reduction of both GO and Au ions. This suspension was then ultrasonicated for 0.5 h and then heated at 333 K for 1 h till evaporation. The sample was then heated at 373 K overnight and annealed at 623 K for 4 h.

Catalyst Characterization

The X-ray powder diffraction patterns of various solids were carried out using a Philips 321/00 instrument. The patterns were run with Ni-filtered Cu K$\alpha$ radiation ($\lambda$=1.541 Å) at 36 kV and 16 mA with scanning speed of 2° in 2 $\theta min^{-1}$. The XRD phases present in the samples were identified with the help of ASTM powder data files.

The surface properties namely BET surface area, total pore volume (Vp) and mean pore radius (r) were determined from $N_2$ adsorption isotherms measured at 77 K using conventional volumetric apparatus. The samples were outgassed at 473 K for 3 h under a reduced pressure of $10^{-5}$ Torr before starting the measurement. The total pore volume was taken from the desorption branch of the isotherm at $p/p^o$=0.98, assuming complete pore saturation.

UV-vis diffuse reflectance spectra of various samples in the 700-300 nm range were obtained using a Jasco V-570 (serial number, C 29635) spectrophotometer, which attached to a diffuse reflectance accessory. The infrared spectra of the samples were recorded in the range of 400-3000 $cm^{-1}$. The method includes mixing few mg of a fine powder of the sample with KBr powder in an agate mortar. The mixture was then pressed by hydraulic press. The transmission was automatically registered against wavenumber ($cm^{-1}$) using a Perkin-Elmer instrument (Spectrum GX), made in USA.

TEM micrographs were measured using a Philips; model Tecani Feil2, at an accelerating voltage of 200 KV. The powder samples were put on carbon foil with a microgrid. TEM images were observed with minimum electron irradiation to prevent damage to the sample structure. SEM (JSM-5200 JEOL, Japan) was used to observe the surface state and structure of the photocatalyst composites. The average particle diameter (d) was calculated by the following formula: d=$\Sigma nidi/\Sigma ni$, where ni is the number of particle diameter di in a certain range, and $\Sigma ni$ is more than 100 nanoparticles on TEM images of the sample.

Cyclohexane Oxidation

All cyclohexane oxidations were carried out; at room temperature, according to the following procedures: 0.05 g of catalyst and 10 mmole cyclohexane were put into a 50 mL photochemical reactor; containing 10 mL of acetonitrile, fitted with a cooling jacket. Addition of 10 mmole $H_2O_2$ (30%) that monitored using iodometric titration was poured into the system continuously and sealed by a rubber septum cap. Samples were then collected every 1 h after switching on the lamp for total photo-oxidation period of 12 hours. These experiments were performed in a closed chamber to avoid interference with ambient lights. The reactor was placed at the centre of the chamber, equipped with a vent for cooling purpose. The UV lamp was horizontally installed inside the UV chamber. The light source emits UV in the portion of the UV spectrum called UV-C (296-390 nm). 125 W UV high pressure mercury lamp fitted with long Teflon tube was inserted into the reaction solution. Samples were collected from the mixture solution at regular intervals and centrifuged. More information on the photo-reactor can be found elsewhere (M. M. Mohamed, S. A. Ahmed, K. S. Khairou, Appl. Catal. B: Environ. 150-151 (2014) 63-73— incorporated herein by reference in its entirety). The samples collected from every experiment using different catalysts were analyzed by GC-MS. GC-MS analyses were performed using a Perkin Elmer Clarus 600C instrument. GC was conducted in the temperature-programming mode, using a SGE BPX5 column (25 m×0.25 mm×0.25 µm). Reaction products were identified by comparison of their retention times with known reference compounds, and by comparing their mass spectra to fragmentation patterns obtained from the NIST spectral library stored in the computer software of the mass spectrometer. Results show that though cyclohexyl hydroperoxide is an important intermediate component formed during the oxidation of cyclohexane, its selectivity is always kept at a very low level in our experiments, far lower than that of cyclohexanone or cyclohexanol, and the main by-products of the reaction were n-butric, n-valeric, succinic, glutaric and adipic acid. To study subsequent reuse of the catalysts, the most recently used catalyst was separated from the reaction mixture, washed in alcohol, dried at ambient temperature, and then put into the next catalytic cyclohexane oxidation run.

Results

Figure 1:
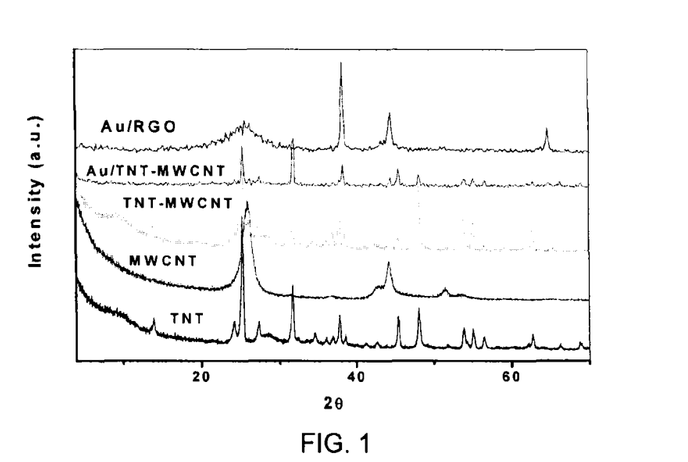
FIG. 1 illustrates XRD patterns of TNT, MWCNT, TNT-MWCNT, Au/TNT-MWCNT and Au/GO.

The XRD patterns (FIG. 1) show gold loaded titanium nanotubes (Au/TNT-inset) as well as gold free one following annealing at 350° C. FIG. 1 shows XRD patterns of TNT, MWCNT, TNT-MWCNT, Au/TNT-MWCNT and Au/GO; the inset is for 3% Au/TNT synthesized using $Na_2S$—$NaBH_4$. The diffraction lines of the annealed TNT exhibit diffraction lines at 2$\theta$ equal 9.5°, 24.01° and 48.4°, representing respectively (002), (0 1 1) and (0 2 0) planes indexed to $Na_2Ti_2O_5.H_2O$ of an orthorhombic lattice (Joint Committee of Powder Diffraction Standards (JCPDS) card no. 47-124) structure. The steady washing by 0.1 M HCl prohibits the massive replacement of $Na^+$ by $H^+$. Accordingly, an appreciable amount of brookite phase is depicted via existence of the characteristic peak at 2$\theta$=30.8°; assigned to the (211) plane, and represents 17% of total phases constituting titania. In addition, this XRD pattern also indicates significant peaks at 2$\theta$=25.3, 38.0, 48.0, 53.8, 55.1 and 62.7° corresponding respectively to (1 0 1), (0 0 4), (2 0 0), (1 0 5), (2 1 1) and (2 0 4) planes, assigned to the anatase phase that constitutes 75% of total phases forming titania. A residual existence of the rutile phase (8%) is observed at 2$\theta$=27.4° and ascribed to the (110) plane. Notably, no significant changes were shown in the structure following gold incorporation via the adopted $Na_2S$—$NaBH_4$ method (seen as inset) reflecting its well dispersion. However, the broad peak at 9.5°; correlated with the interlayer distance $d_{200}$ in the nanotubes wall, is almost vanished in the 3% Au/TNT sample proposing slight distortion of the crystalline order within the layers due to the ion-exchange process. In this concern, $NaBH_4$ might be responsible for reducing some exposed OH moieties on the titanate surfaces. The mean particle size of TNT diffraction peak at 2$\theta$=25.3° shows higher crystallite growth than that of TNT containing gold suggesting smaller crystallites size of the latter comparatively.

In order to prepare high activity photocatalysts, multi-walled carbon nanotube (MWCNT) is added to TNT for modifying the latter photocatalyst. The peaks ascribed to MWCNT cannot be detected; confirming its dispersion in the nanocrystalline structure of TNT. However, the residual peak at 2$\theta$=26.5°; well indexed to the 002 reflection of graphitic carbons, coincided with that of MWCNT at the same diffraction angle is shown i.e. TNT almost cover the whole surface of MWCNT. Interestingly, the enhancement of anatase crystallinity is noticed via increasing their peak intensities. Small peaks at 2θ=38.4 and 44.4° are detected for Au⁰ corresponding to (111) and (200) phases on the Au/TNT-MWCNT sample. This latter sample also showed a marked decrease in intensities of all diffraction lines assigned to anatase/TNT phase in favour of the brookite one via exposing the peak at 30.8°. The peaks intensity decrement in Au/TNT-MWCNT further depict that TNT-MWCNT is homogenously covered by the Au nanoparticles, reducing the contact between the $TiO_2$ particles and thus decreases their particles size. This Figure also shows the XRD pattern of Au/RGO. It proves that GO is reduced to graphene during the treatment with hydrazine hydrate (G. M. Lu, D. Ji, G. Qian, Y. X. Qi, X. L. Wang, J. S. Suo, Appl. Catal. A: Gen. 280 (2005)175-180—incorporated herein by reference in its entirety) via illustrating a broad peak at 2θ=25.8° corresponding to interlayer distance of 3.53 Å. The XRD peaks belonging to Au nanoparticles are detected in Au/RGO at 2θ=38.5, 44.4 and 64.5° corresponding respectively to (111), (200) and (311) sites. These characteristic peaks distinguish fcc structure of gold nanoparticles (Joint Committee on Power Diffraction Standard (JCPDS), File No. 04-0784) of polycrystalline nature. A comparison between Au/RGO and Au/TNT-MWCNT indicates that Au was mainly exposed on the surface of the former where it was well dispersed on that of the latter.

Figure 2A:
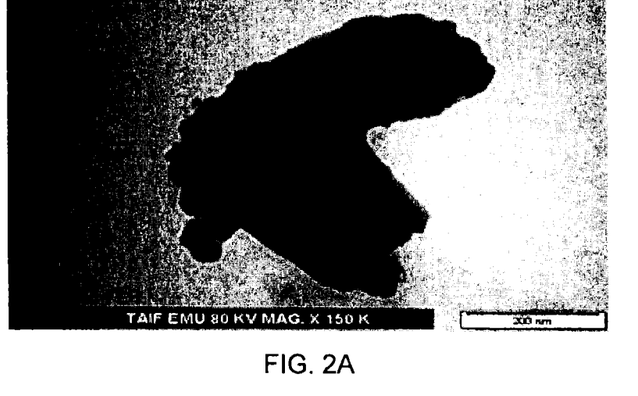
FIGS. 2A-2C are TEM images Au/TNT, Au/TNT-MWCNT and Au/RGO.
Figure 2B:
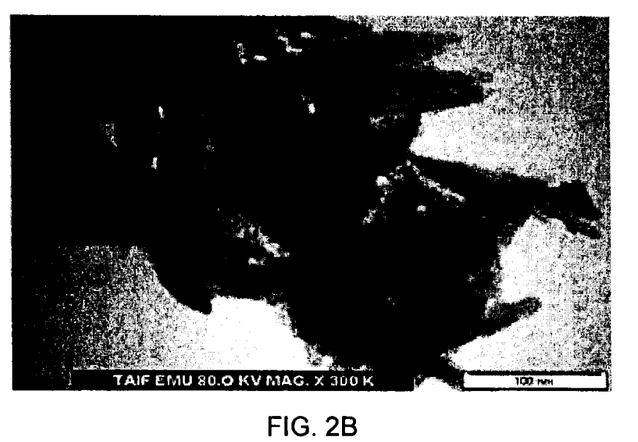
Figure 2C:
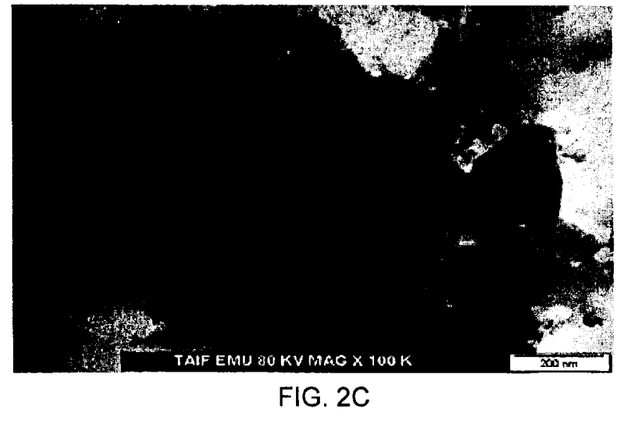

FIG. 2A shows a TEM Image of 3% Au/TNT annealed at 623 K; the inset is for pure TNT. FIG. 2B shows a TEM image of 3% Au/TNT-MWCNT annealed at 623 K; the inset is for the HRTEM of Au nanoparticles (traced by the red arrow) and HRTEM of MWCNT is in the lower part of the image. FIG. 2C shows a TEM Image of 3% Au/RGO annealed at 573 K; the inset is TEM of RGO. The TEM image of the 3% Au/TNT sample annealed at 573 K shows a tubular structure with an average diameter of 50 nm and length equal 200 nm (FIG. 2A). It seems that the tubular structure is partly damaged as it appears at the peripheral part of the image via the presence of spherical nanoparticles. The dark field TEM image seen as in-set elaborates the agglomeration of Au free TNT sample. This conglomeration is decreased relatively following Au incorporation. The incorporation of MWCNT with 3% Au/TNT affects the tubular structure seen in 3% Au/TNT and changes it into spindle-like shape (FIG. 2B). This image shows an average particle diameter of 15 nm and length equal 60 nm. As it appears, MWCNT affects the TNT shape and thus decreasing both the diameter as well as the length compared with 3% Au/TNT, proposing an exhibited interaction between MWCNT and TNT. In addition, the agglomeration is decreased upon addition of MWCNT proposing that the latter could also act as a spacer for TNT particles. The in-set image of Au nanoparticle; of hexagonal shape and 15 nm diameter, proposes that Au atoms are mainly not incorporated inside TNT but most probably localizes on its surface. In the lower part of the image, CNTs are also exhibited as free standing transparent nanotubes as depicted by HRTEM indicating that some of them are not well incorporated with TNT. The TEM image of the 3% Au/RGO sample (FIG. 2C) illustrates that the morphology of RGO is consisting of thin stacked flakes made up of well-defined layers. They show a homogeneous dispersion of Au nanoparticles of circular shape and average diameter of 25 nm in the reduced GO (RGO) matrix, as seen in the inset FIG. 2. The Au nanoparticles are not simply mixed up or blended with RGO; rather they are dispersed on the RGO sheets.

The FTIR spectra of oxidized MWCNTs and MWCNTs/TNTs composite are measured to comprehend their interconnection (see supporting information). Bands at 1575, 1653 and 1713 $cm^{-1}$ attributed to C=C, carbonyl and carboxyl, respectively are exhibited for MWCNT. In addition, an ester group localized as a strong band at 1175 $cm^{-1}$ is depicted. The FTIR spectrum of MWCNT-TNT shows a peak at 700 $cm^{-1}$ due to Ti—O—Ti vibration beside those exhibited for carbonyl and unsaturated carbon depicted before. The band intensity in the region of the asymmetric carboxylate stretching mode at 1400 $cm^{-1}$ is much higher than that in MWCNT. This assumes that the carboxylate oxygen of CNT interacts with the titanium ion (M. M. Ibrahim, S. A. Ahmed, K. S. Khairou, M. M. Mohamed Appl. Catal. A: General 475 (2014) 90-97; L. Fuks, D. Filipiuk, M. Majdan, J. Mol. Struct. 792-793 (2006) 104-109—incorporated herein by reference in its entirety) provoking the Ti—O—C bond formation. This result ascertained the hyposis about the possible interaction between TNT and MWCNT moieties.

Figure 3A:
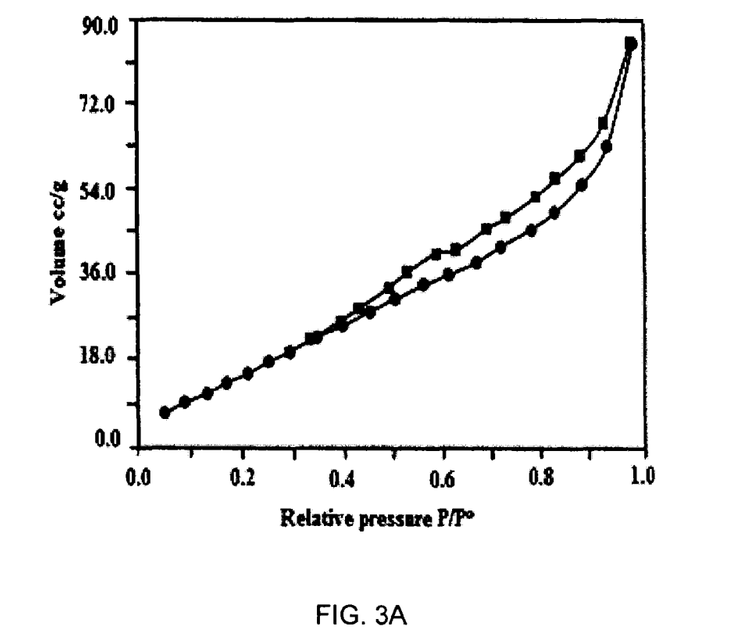
FIGS. 3A-3B are graphs of the adsorption-desorption isotherm of the Au/RGO sample and the Au/TNT-MWCNT sample.
Figure 3B:
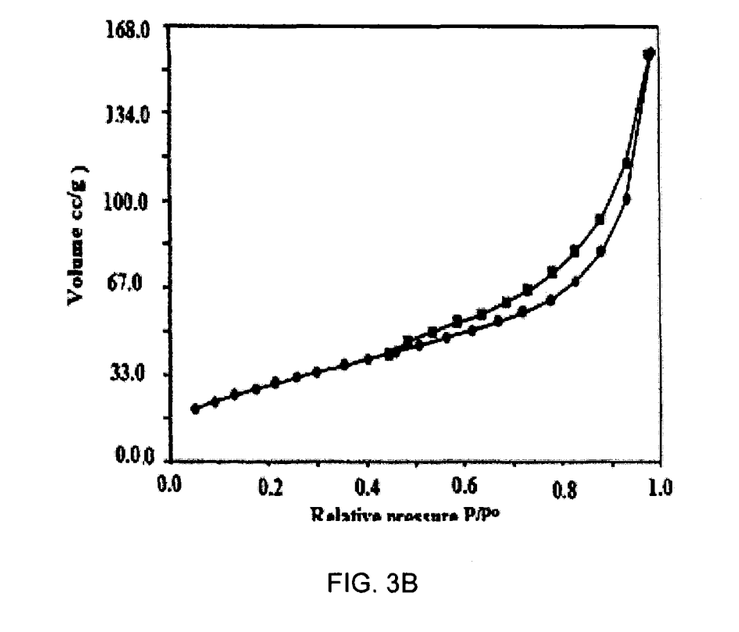

FIG. 3A and FIG. 3B present the $N_2$ adsorption-desorption isotherms of Au/RGO and Au/TNT-MWCNT, as representative samples, heated at 623 K. FIG. 3A shows the adsorption-desorption isotherm of the Au/RGO sample. FIG. 3B Adsorption-desorption isotherm of the Au/TNT-MWCNT sample They showed type II isotherms with H3 hysteresis loops according to IUPAC [48] classification. The initial part of the isotherm is attributed to monolayer-multilayer adsorption. The Type H3 hysteresis loop observed is characteristic to aggregates of plate-like or slit-shaped pores (J. M. Herrmann, W. Mu, P. Pichat, Stud. Surf. Sci. Catal. (1991) 405-414—incorporated herein by reference in its entirety). The surface properties of synthesized samples determined by $N_2$ adsorption-desorption measurements are presented in Table 1. Table 1 is presented below.

TABLE 1

Surface texturing properties of the synthesized catalysts

| Sample name | $^a$BET Surface area $m^2/g$ | $^b$Pore volume Vp $Cm^3/g$ | $^c$Average pore diameter r nm |
|---|---|---|---|
| TNT | 72.9 | 0.135 | 19.5 |
| TNT-MWCNT | 141 | 0.180 | 17.9 |
| Au/TNT | 90 | 0.146 | 18.6 |
| Au/TNT-MWCNT | 194 | 0.192 | 17.5 |
| Au/RGO | 78.4 | 0.30 | 15.3 |

Notes
$^a S_{BET}$; BET Surface Area,
$^b$Vp; Pore Volume,
$^c$r; BJH Adsorption average pore diameter.

The specific surface area, pore volume and pore radius of Au/RGO is determined to be 78.5 $m^2/g$, 0.3 $cm^3/g$ and 15.3 nm, respectively. The hysteresis loop of the latter sample closes at lower relative pressures $P/P^o$ equal 3.5. This signifies the presence of large pores that ascertained from increasing the pore radius into 15.3 nm. For TNT, the isotherm (not shown) is also of type II with a $N_2$ hysteresis-loop, characteristic of mesoporous materials, and discloses a specific surface area equal 72.9 $m^2/g$. The presence of Au in TNT led to a significant increase in $S_{BET}$ comprised of 23% compared to TNT. Incorporation of MWCNTs into TNT led to a marked increase in surface areas as twice that of the later, as shown in Table 1. Accordingly, the pore volume of TNT-MWCNT showed a marked increase equal 0.180 cm$^3$/g compared to 0.135 cm$^3$/g for TNT, proposing the enforcement of MWCNTs inside TNT pore structure. The noticed increase in the pore volume of Au/TNT-MWCNT into 0.192 cm$^3$/g might indicate the well incorporation of Au into the TNT(MWCNT) pores. Accordingly, the average pore diameter showed a decrease in the following order: TNT (19.5 nm)>TNT-MWCNT (17.9 nm)>Au/TNT-MWCNT (17.5 nm). Taking into consideration that the average inner diameter of TNTs determined from TEM measurements was in the range of 30-60 nm hence, the method of nitrogen adsorption down estimates the average diameter of nanotubes. Accordingly, N$_2$ adsorption method accounts for the pores inside the tubes rather than the pores between the tubes. These external pores are usually bigger than the internal pores and the size of these pores depends on the way the nanotube agglomerates into bundles. The adsorption-desorption isotherm of Au/TNT-MWCNT performed by N$_2$ adsorption at −197° C. confirms that the N$_2$ adsorption isotherm is belong to type II, in the IUPAC classification. The non-limiting adsorption at high P/P$^o$ is characteristic of Type H3 i.e. no limiting adsorption at high P/Po.

Figure 4:
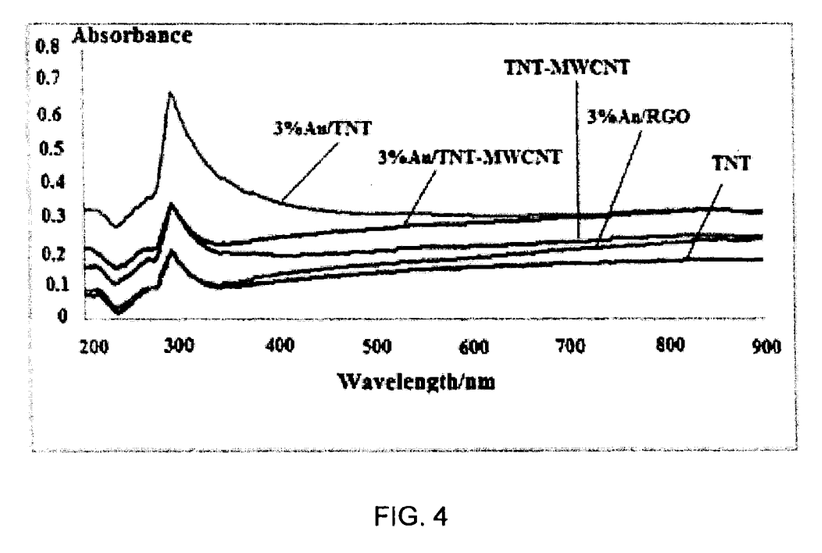
FIG. 4 illustrates a UV-Vis adsorption spectra of TNT, TNT-MWCNT, Au/TNT-MWCNT, Au/TNT and Au/RGO samples.

The light absorption properties of Au containing samples including Au/TNT, Au/TNT-MWCNT and Au/RGO are analyzed by UV-Vis diffuse reflectance spectroscopy (FIG. 4) in comparison with Au free ones including TNT and TNT-MWCNT samples. FIG. 4 shows a UV-Vis absorption spectra of TNT, TNT-MWCNT, 3% Au/TNT-MWCNT, 3% Au/TNT and 3% Au/RGO samples. TNT absorption threshold is localized between 260 and 340 nm with a maximum at 290 nm. On the other hand, the Au/RGO sample coincides with that of TNT sample in the UV margin but it shows a shift towards the visible light region. On the other hand, the 30% MWCNT-TNT composite absorbs much more light both in UV and visible regions compared with TNT and Au/RGO samples. This indicates that the introduction of CNT to TNT results in an increment of surface electric charge of the later. Loading Au on TNT-MWCNT did not change the absorptivity in the UV region of TNT-MWCNT but enhances that of visible light via the noticed linear increase towards the visible light till 900 nm. This suggests that the morphologies of Au such as particle size, shape and crystallinity are different from those in the Au/RGO sample, as confirmed from XRD and TEM investigations. In agreement, Au/RGO, Au/TNT-MWCNT and Au/TNT displayed a marked absorption enhancement both in visible-light and ultraviolet regions, and extended the margin of UV from 260 to 400 nm. The absence of surface plasmon resonance of Au NPs albeit changing the samples colour; from white for TNT to violet in Au/TNT, dark blue in Au/TNT-MWCNT and black in Au/RGO, could be caused by the changing of their surrounding environment (A. Maldotti, A. Molinari, R. Amadelli, Chem. Rev. 102 (2002) 3811-3836—incorporated herein by reference in its entirety). This could also be due to lowering the gold content and/or deposition of the substrate on the gold nanostructures (J. Ho, H. Jia, Analytica Chimica Acta 651 (2009) 91-97—incorporated herein by reference in its entirety).

The photocatalytic performance of Au based catalysts is evaluated in the selective oxidation of cyclohexane with hydrogen peroxide and the reaction results are summarized in

TABLE 2 catalytic properties in selective oxidation of cyclohexane

| catalyst | Cyclohexane conversion (%) | $^a$Products selectivity (%) | | | $^b$K/A ratio | $^c$By-products | $^d$Activity (mmole g$_{cat}^{-1}$ min$^{-1}$) |
|---|---|---|---|---|---|---|---|
| | | Cyclohexaol H$_2$O$_2$ | Cyclohexanone | | | | |
| TNT | 2.1 | 51 | 32 | | 0.63 | 17 | 0.00097 |
| | | 38.2 | | | | | |
| TNT-MWCNT | 3.2 | 35 | 50 | | 1.43 | 15 | 0.0015 |
| | | 40.3 | | | | | |
| Au/TNT | 4 | 30 | 55 | | 1.83 | 15 | 0.0019 |
| | | 34 | | | | | |
| Au/TNT-MWCNT | 7.5 | 20 | 75 | | 3.75 | 5 | 0.0035 |
| | | 22 | | | | | |
| Au/RGO | 6 | 28 | 60 | | 2.14 | 12 | 0.0028 |
| | | 37 | | | | | |

Figure 5:
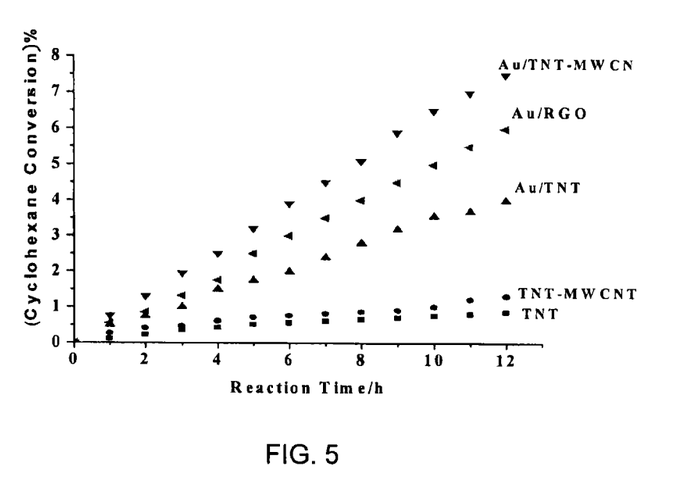
FIG. 5 is a graph of cyclohexane conversion v time on stream on TNT, TNT-MWCNT, Au/TNT, Au/RGO and Au/TNT-MWCNT catalysts.

All reactions were done with 0.05 g of catalyst, 10 mmol cyclohexane, 10 mmol H$_2$O$_2$, 10 mL of acetonitrile, photoirradiation time, 12 h (>256 nm).
$^a$Selectivity (%) of product = [(concentration of product) × (total concentration of all products) − 1] × 100.
$^b$K/A: the mole ratio value of cyclohexanone to cyclohexanol
$^c$By-products are mainly ring-opened acids such as n-butric, n-valeric, succinic, glutaric and adipic acid
$^d$The average rate for 12 h of reaction time
H$_2$O$_2$ correspond to the amount consumed in the reaction Under the same reaction conditions, no conversion is observed in the absence of catalyst but all other reaction components present confirmed that the catalysis is intimately involved with Au as well as with TNT (FIG. 5). FIG. 5 shows a graph of the cyclohexane conversion vs. time on stream on TNT, TNT-MWCNT, Au/TNT, Au/RGO and Au/TNT-MWCNT catalysts. The experimental conditions were kept constant at the following reaction conditions: All reactions were done with 0.05 g of catalyst, 10 mmol cyclohexane, 10 mmol H$_2$O$_2$, 10 mL of acetonitrile, photoirradiation time, 12 h (>296 nm). This indicates that that gold-based catalysts may be active in initiating the cyclohexane oxidation reaction. On the other hand, TiO$_2$ showed some activity also towards the same reaction and most importantly the hydroxyl group density on its surface, which used to take a major high part in this reaction (P. Du, J. A. Moulijn, G. Mul. Journal of Catalysis 238 (2006) 342-352—incorporated herein by reference in its entirety). Catalysts Au/TNT-MWCNT and Au/RGO exhibited the highest activity and selectivity with a conversion equal 7.5 and 6%, respectively after 12 h reaction.

Figure 7:
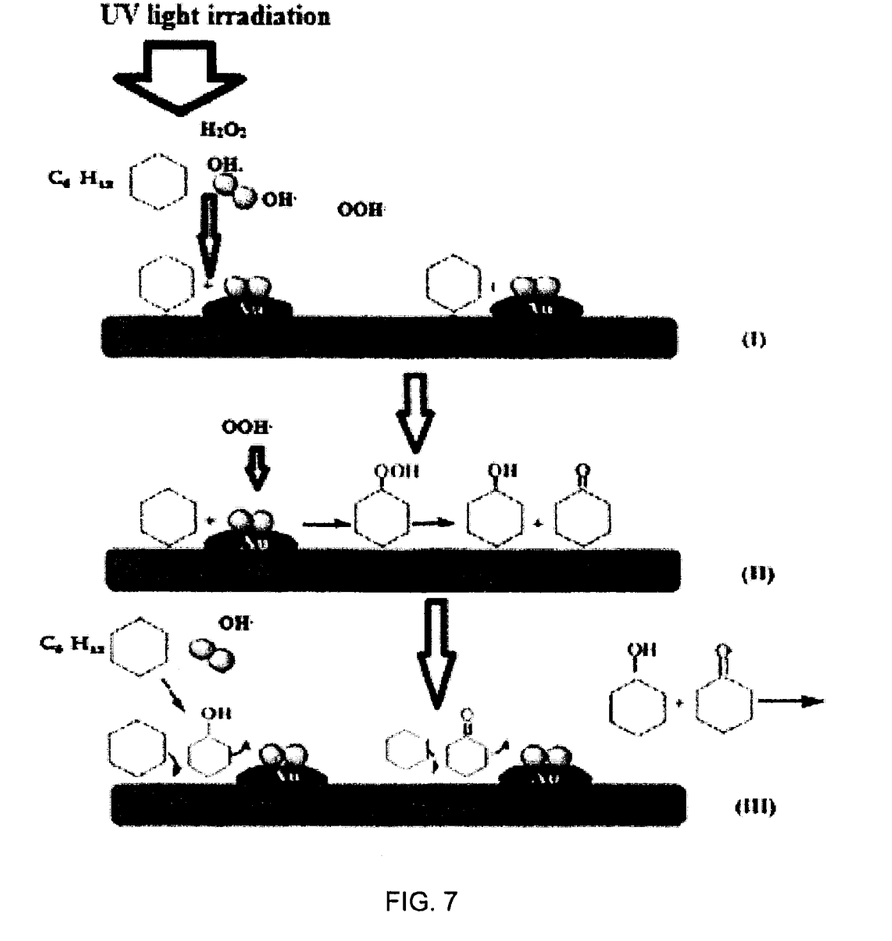
FIG. 7 illustrates the oxidation of cyclohexane on catalyst Au/TNT-MWCNT.

The Au/TNT-MWCNT catalyst exhibited a conversion of almost double that of Au/TNT. This indicates that MWCNT takes part in this reaction i.e., the morphological and structure order of carbon nanotubes are factors affecting the adsorption of organic moieties. The selectivity of cyclohexanone and cyclohexanol over Au/TNT-MWCNT was as high as 3.75 (K/A ratio) exceeding those on Au/RGO (2.14), Au/TNT (1.83) and TNT-MWCNT (1.43) catalysts. On the contrary, TNT exhibited the lowest K/A ratio (0.63) due to the absence of Au nanoparticles. It can be seen from FIG. 5 that the conversion increases with time together with cyclohexanone selectivity (Table 2). Interestingly, enhancing the conversion of TNT compared with other mentioned $TiO_2$ catalysts (K. Shankar, J. I. Basham, N. K. Allam, O. K. Varghese, G. K. Mor, X. Feng, Maggie Paulose, J. A. Seabold, Kyoung-Shin Choi, C. A. Grimes J. Phys. Chem. C 113 (2009) 6327-6359—incorporated herein by reference in its entirety) could be due to the mesoporous character of TNT surface that maximized the adsorption of the non-polar cyclohexane molecules as well as to the enhanced photocatalytically active anatase sites. On the other hand, the open tubular structure of TNT offered a much higher contact area as well as a facile diffusion of $H_2O_2$ via forming complex with $TiO_2$ nanotubes of high Lewis acidity (P. Wu, P. Baia, K. P. Loh, X. S. Zhao, Catalysis Today 158 (2010) 220-227—incorporated herein by reference in its entirety). This response towards $H_2O_2$ is even increased when Au nanoparticles are embedded in the pores of $TiO_2$ nanotube, via constructing a metal-semiconductor heterojunction (J. T. Carneiro, J. A. Moulijn, G. Mul, Journal of Catalysis 273 (2010) 199-210—incorporated herein by reference in its entirety). Under illumination, the electric potential difference generated on the interface of $Au/TiO_2$ nanotube heterojunction assisted the separation of the photogenerated hole—electron pair i.e. quicken the transferring rate of the holes and resulting in an enhanced photo-oxidation activity. Data shown in Table 2 confirmed the enhancement of cyclohexane oxidation rate on Au/TNT-MWCNT (0.0035 mmole $g^{-1}$ $min^{-1}$) to a higher cyclohexanone production together with lowering the non-selective bi-products formed. Gold catalysts are inefficient in promoting hydrocarbon oxidation by oxygen due to the lack of coordination of hydrocarbons with Lewis acid sites (C. B. Almquist, P. Biswas, Appl. Catal. A—Gen. 214 (2001) 259-271—incorporated herein by reference in its entirety). However, on correlating the catalytic performance with the catalyst structure properties, Au nanoparticles) ($Au^0$) may be the active sites for the cyclohexane oxidation and the particles size played an important role in the reaction. Catalyst Au/TNT-MWCNT with an average Au particle size of 15 nm of hexagonal structure showed a higher activity than Au/RGO that exposed Au nanoparticle of 25 nm average size. This may be due to decreasing Au particles size induces an increase in Au atoms density active surface. This indeed will favour the adsorption and activation of oxygen molecule of $H_2O_2$ during the oxidation reaction. The observed superior catalytic properties of the catalyst Au/TNT-MWCNT may be related not only to the Au particle size, but also to the surface properties of the support. As cyclohexane is a non-polar organic compound, a preferred adsorption into the hydrophobic MWCNT surface parts is more favorable. On the other hand, $H_2O_2$ molecules are adsorbed and activated by Au nanoparticles (M. M. Mohamed, M. T. Salama, M. Ichikawa, J. Colloid Interface Science Sci, 224 (2000) 366-371—incorporated herein by reference in its entirety). After irradiation of 12 h under a 125 W of middle-pressure mercury lamp, the oxidation rate of cyclohexane using the Au/TNT-MWCNT catalyst was the best between the synthesized catalysts. By performing a thorough product analysis of the cyclohexane oxidation reaction under the relevant conditions it is found that gold-based catalysts do not show high ICA selectivities (>90%) at high conversions (>7%) as is reported in open literatures (H. Zhang, P. X. Feng, Carbon 4 8 (2 0 1 0) 3 5 9-3 6 4; A. W. Musumeci, E. R. Waclawik, R. L. Frost, Spectrochim Acta Part A 71 (2008) 140-142—each incorporated herein by reference in its entirety). The cyclohexane oxidation by Au-based catalysts described herein is inconsistent with the above-mentioned results. This based on the roles played by TNT and MWCNT in activating and initiating electrons and holes assisted by photo irradiation as well as the absorbability evoked by the nanocarbon. More clarification on the contribution of both $Au/TiO_2$ (TNT) and MWCNT towards cyclohexane oxidation may be due to other factors. An electron—hole pair can be produced between the valence and conduction band of TNT (W. Yongmei, J. Zhang, L. Xiao, F. Chen, Appl. Catal. B: Environ. 88 (2009)525-532—incorporated herein by reference in its entirety). The photogenerated electrons can be trapped by MWCNT, holding up the recombination process. The trapped electrons may be further transferred to oxygen (W. Su, S. S. Wei, S. Q. Hu, J. X. Tang, J. Hazard. Mater. 172 (2009) 716-720—incorporated herein by reference in its entirety), which is adsorbed on the TNT surface, to generate superoxide radical as well as hydroperoxy ($HO_2$.) and hydroxyl (OH.) radicals produced via $H_2O_2$ adsorption. Accordingly, the holes or the produced hydroxyl radicals are the oxidizing agents in cyclohexane oxidation. The interface between Au and TNT may form an electrical barrier, resulting in the transfer of electrons into Au (T. Harifi, M. Montazer, Applied Catalysis A: General 473 (2014) 104-115—incorporated herein by reference in its entirety). In addition, increasing the $S_{BFT}$; and pore volume (0.192 $cm^3/g$), of Au/TNT-MWCNT to 194 $m^2/g$ affects cyclohexane conversion to be the best comparatively. Concurrently, although Au/RGO exhibited an increase in the pore volume value (into 0.30 $cm^3/g$), it presents lower activity than that of the latter due to the decrease in $S_{BFT}$ value into 78 $m^2/g$ as well as to the absence of TNT structure responsible for light absorption. As illustrated in FIG. 7, $H_2O_2$ molecules are adsorbed and activated by Au nanoparticles while cyclohexane molecules preferred the hydrophobic part of MWCNT surface (Step I). Reaction between the adsorbed cyclohexane and dissociated $H_2O_2$ produced intermediate cyclohexyl hydroperoxide, which decomposed to form cyclohexanol and cyclohexanone adsorbed on the catalyst (Step II). These oxidation products can be further oxidized to byproducts, such as n-butric, n-valeric, succinic, glutaric and adipic acid if they do not desorb from the surface promptly. Cyclohexane is preferentially adsorbed over cyclohexanol and cyclohexanone by the Au/TNT-MWCNT catalyst because of the surface hydrophobicity of the catalyst (Step III), thus reducing the probability of deep oxidation.

Although gold-based catalysts play a role in directing the oxidation mechanism, the reaction proceeds through a radical-chain mechanism. A radical-chain mechanism explains the slow initiation of the oxidation reaction by the gold-based catalysts at the very beginning. Since initiation proceeds through a Haber-Weis cycle, the initiation rate strongly depends on the redox potential of the metal. In this regard, gold is not likely to be an efficient initiator. Affirming that the reaction proceeded via a radical chain mechanism the hydroquinone (HQ) is used to accomplish whether or not it is a radical involved reaction. At 270 min on stream when the conversion of 2.5% is reached for catalyst Au/TNT- MWCNT, a specific amount of HQ (0.4 g dissolved in a 1:1 CyH: acetonitrile mixture) is added. It is shown that the amount of products in the liquid phase remained constant between 285 and 300 min (0.5% conversion) on stream then the cyclohexane conversion is completely inhibited. The strong yellow colour of the liquid-phase samples after HQ addition indicated the formation of benzoquinone, confirming that the reaction proceeds via free radical mechanism. The decomposition of $H_2O_2$ generates HOO. and HO. over gold metal as well as on TNT (A. Reina, X. T. Jia, J. Ho, D. Nezich, H. Son, V. Bulovic, Nano Lett 9(1) (2009)30-35; A. C. Ferrari, Solid State Commun. 143 (2007) 47-51—each incorporated herein by reference in its entirety); as explained previously. Such radicals abstract hydrogen from cyclohexane forming cyclohexyl radicals. This unstable peroxide dissociates via two separate processes to give cyclohexanol and cyclohexanone.

When the amount of $H_2O_2$ increased to 15 mmole (keeping all other factors constant) the conversion of cyclohexane increases. The increase in the amount of oxidant helps in generating more radicals and thereby increasing the conversion of Au/TNT-MWCNT into 9.0% with effective use of $H_2O_2$ reaching 42%. The selectivity of cyclohexanone increases into 85% while that for cyclohexanol decreases. This might be due to oxidation of cyclohexanol to cyclohexanone in the presence of excess amounts of $H_2O_2$. However, exceeding the amount of $H_2O_2$ into 20 mmol causes a reaction termination and thus the efficiency of $H_2O_2$ decreases into 33%.

Figure 6:
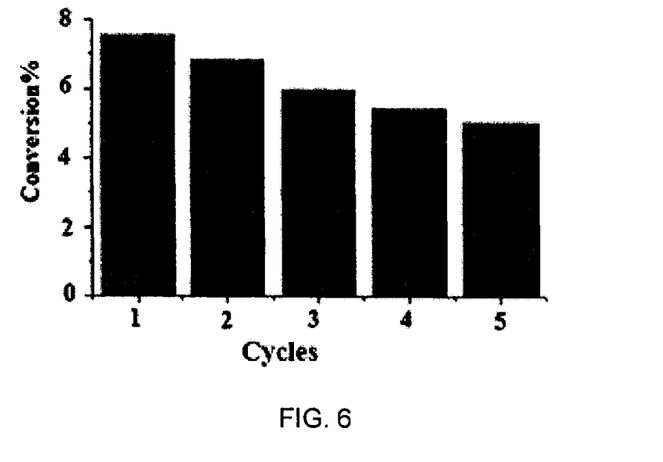
FIG. 6 is a graph illustrating the conversion yield of cyclohexane of repeated cycles up to 5 times of the Au/TNT-MWCNT photocatalyst.

The regenerated catalyst showed only a little decrease in the conversion of cyclohexane following the fifth run, as shown in FIG. 6. FIG. 6 is a graph of the repeated cycles up to 5 times illustrating the conversion yield of cyclohexane after 12 h over the Au/TNT-MWCNT photocatalyst. The experimental conditions were kept constant at the following reaction conditions: All reactions were done with 0.05 g of catalyst, 10 mmol cyclohexane, 10 mmol $H_2O_2$, 10 mL of acetonitrile, photoirradiation time, 12 h (>296 nm). It shows a decrease from 7.5 into 5.7% conversion proposing the intact of active sites even after this long period that extends into 60 h. The recovered supported catalyst attained via filtration is only washed with acetonitrile and dried at 50° C. for 2 h before further use in the next run. The presence of different types of sites on the catalyst surface can be considered. These could be related to the titanium nanotube that acts as Lewis acid sites; due to their low coordination, as well as light harvesting together with gold nanoparticles are considered as strong adsorption sites, suitable for both cyclohexane and $H_2O_2$ moieties. The second type could be the hydrophobic MWCNT that was associated with cyclohexane adsorption in the first place.

Gold nanoparticles (15 nm, hexagonal shape) dispersed on TNT-MWCNT composites prepared by hydrothermal deposition method exhibited higher photocatalytic (125 W, λ=296-400 nm) activity for cyclohexane oxidation; in liquid phase, (Conversion=7.5%) and k/A oil selectivity exceeding Au/RGO and Au/TNT catalysts. The oxidation of cyclohexane into the main products, cyclohexanone and cyclohexanol, on the former catalyst was used repeatedly for at least five times without significant loss in either conversion or selectivity values. This was attributed to the uniform dispersion of Au nanoparticles on the mesoporous TNT support, enhancement of cyclohexane adsorption onto the MWCNT hydrophobic surface and to the surface texturing properties of the composite TNT-MWCNT. A competing adsorption and desorption mechanism was used to explain the high K/A oil selectivity on the catalyst prepared using the mentioned method. One should state that improving the capability of this new kind of catalyst demands more in-depth experimental work to enhance the activity. More important correlations about the mechanism and the activity of the catalysts in view of their performances under UV illuminations with the experimental results were developed and discussed.

In one embodiment the gold nanoparticles (15 nm, hexagonal shape) dispersed on TNT-MWCNT composites prepared by hydrothermal deposition method exhibited higher photocatalytic (125 W, λ=296-400 nm) activity for cyclohexane oxidation; in liquid phase, (Conversion=7.5%) and k/A oil selectivity exceeding Au/RGO and Au/TNT catalysts. The oxidation of cyclohexane into the main products, cyclohexanone and cyclohexanol, on the former catalyst was used repeatedly for at least five times without significant loss in either conversion or selectivity values. This was attributed to the uniform dispersion of Au nanoparticles on the mesoporous TNT support, enhancement of cyclohexane adsorption onto the MWCNT hydrophobic surface and to the surface texturing properties of the composite TNT-MWCNT. A competing adsorption and desorption mechanism was used to explain the high K/A oil selectivity on the catalyst prepared using the mentioned method. One should state that improving the capability of this new kind of catalyst demands more in-depth experimental work to enhance the activity.

Photocatalytic oxidation of neat cyclohexane (CHA) with $H_2O_2$ as an oxidant was carried out using gold modified several types of materials including titanium nanotube (Au/TNT), reduced graphene oxide (Au/RGO) as well as titanium nanotube—multiwalled carbon nanotube composites (Au/TNT-MWCNT) under UV irradiations (125 W, λ>296 nm). The synthesized nanoparticles were characterized using physical adsorption of nitrogen, X-ray diffraction, transmission electron microscopy and ultraviolet—visible diffuse reflectance spectroscopy and the reaction products were analyzed by GC-MS. Both Au/RGO and Au/TNT-MWCNT catalysts promoted partial CHA oxidation with high conversion (6-7.5%) and selectivity (60-75%); to cyclohexanone, exceeding Au/TNT, TNT-MWCNT and TNT catalysts (cony. 2.1-4%, sel. 32-55%). Au/TNT-MWCNT synthesized using hydrothermal deposition method exhibited the highest catalytic activity. This was chiefly attributable to the high surface hydrophobicity of MWCNT that accelerated CHA adsorption, bonding of cyclohexanol and cyclohexanone to TNT as well as decomposition of $H_2O_2$ on gold nanoparticles. Increasing the surface area as well as decreasing the average particle size of $Au^0$ to 15 nm of hexagonal shape contributed to the high catalytic activity of Au/TNT-MWCNT in achieving turnover frequency of 0.0035 mmole$^{-1}$g$^{-1}$ min$^{-1}$ and yield of 7.5%, after 12 h reaction time. The later catalyst exceeded that industrially synthesized based on Co catalysts (3.6%) at high temperatures. For confirming the autoxidation process, a radical scavenger offered a proof that the oxidation follows a radical-chain mechanism. The differences in surface morphology, light absorption and surface properties of Au/TNT when incorporated with MWCNT were well investigated. The influence of the latter on the activity and recyclability of Au/TNT has maintained almost the same level of activity after the fifth cycles.

Thus, the foregoing discussion discloses and describes merely exemplary embodiments of the present invention. As will be understood by those skilled in the art, the present invention may be embodied in other specific forms without departing from the spirit or essential characteristics thereof.

Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method for oxidation of cyclohexane, comprising:
   reacting cyclohexane in a photocatalytic oxidation reaction in the presence of a solution of $H_2O_2$ and a gold titanium nanotube-multiwalled carbon nanotube composite, comprising:
   30-40 weight % multi-walled carbon nanotubes and 60-70% weight % titanium nanotubes, each based on the total weight of the titanium nanotubes and the multiwalled carbon nanotubes; and
   2-4 weight % of Au based on the total weight of the nanotube composite, wherein the Au is located in at least one wall of the titanium nanotube and wall of the multiwalled carbon nanotube.

2. The method of claim 1, wherein 0.02-0.10 g of the nanotube composite is employed per 10 mmol of cyclohexane.

3. The method of claim 1, wherein the solution of $H_2O_2$ has a concentration in the range of 10-40%.

4. The method of claim 1, wherein the nanotube composite has an average particle diameter of 10-20 nm.

5. The method of claim 1, wherein the nanotube composite has a surface area of 50-500 $m^2/g$.

6. The method of claim 1, wherein the nanotube composite has a pore volume of 0.180-0.199 $cm^3/g$.

7. The method of claim 1, wherein the nanotube composite has a spindle shape.

8. The method of claim 1, wherein the nanotube composite has 3-3.5 weight % of Au based on the total weight of the nanotube composite.

9. The method of claim 1, wherein the nanotube composite comprises 30% by weight of the multi-walled carbon nanotube and 70% by weight of the titanium nanotube, each based on the total weight of the titanium nanotubes and the multiwalled carbon nanotubes.

* * * * *